United States Patent [19]
Hyman

[11] 4,114,144
[45] Sep. 12, 1978

[54] AUTOMATIC AIR-IN-LINE FLUID DETECTOR

[75] Inventor: Oscar E. Hyman, Encinitas, Calif.

[73] Assignee: Imed Corporation, San Diego, Calif.

[21] Appl. No.: 713,664

[22] Filed: Aug. 12, 1976

[51] Int. Cl.$^2$ ............................................. G08B 21/00
[52] U.S. Cl. ................................. 340/632; 73/194 E; 128/214 E; 128/DIG. 13; 356/39
[58] Field of Search ............... 340/239 R; 128/214 E, 128/214 F, DIG. 13; 73/194 E; 356/39

[56] References Cited

U.S. PATENT DOCUMENTS

| | | | |
|---|---|---|---|
| 3,618,061 | 11/1971 | Livers | 340/239 R |
| 3,699,560 | 10/1972 | Meunier | 340/239 R |

*Primary Examiner*—John W. Caldwell, Sr.
*Assistant Examiner*—Daniel Myer

*Attorney, Agent, or Firm*—Charles H. Schwartz

[57] ABSTRACT

An automatic air-in-line detector for either a transparent or an opaque fluid including first detector means for detecting air-in-line in the transparent fluid and second detector means for detecting air-in-line in the opaque fluid, and additionally including control means coupled to the first and second detector means and automatically responsive to the difference between the transparent fluid and the opaque fluid for enabling the first detector means in response to the transparent fluid and for enabling the second detector means in response to the opaque fluid and with an alarm in accordance with the detection of air-in-line in either the transparent or opaque fluid. If any of the detectors fail, the system either automatically alarms or becomes more sensitive. If the control means fail, the system automatically alarms.

23 Claims, 8 Drawing Figures

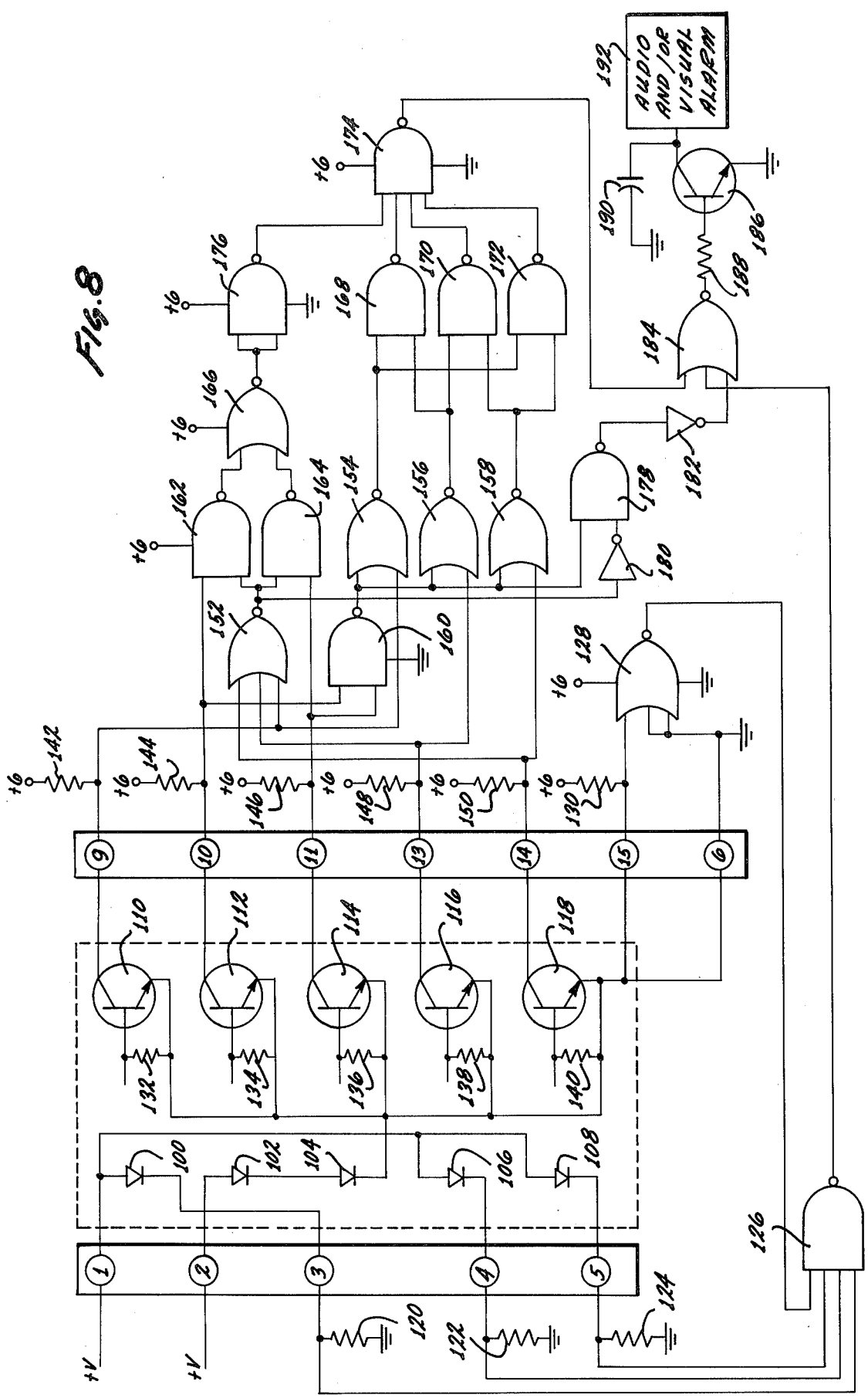

AUTOMATIC AIR-IN-LINE FLUID DETECTOR

The present invention is directed to an automatic air-in-line fluid which automatically discriminates between a transparent fluid such as a typical intravenous drug solution and an opaque fluid such as blood and in addition to the discrimination between the two types of fluid provides for an automatic detection of air-in-line whether the fluid is transparent or opaque.

During the infusion of a fluid into a patient, it is important that a minimum amount of air be included with the infusion of the fluid. A small amount of air which occurs with relatively small air bubbles are permissible but air bubbles greater than a particular size are not permissible since such air when infused into the patient could be extremely dangerous.

The newest methods of infusing fluid to a patient use a pump so as to provide for the infusion of fluid in the patient on a positive basis. The pump may be used to infuse the patient with a typical intravenous solution, such as a drug solution or the pump may be used to pump blood to the patient. In the past, such pumps have been provided with a detector to detect for the presence of air in the fluid line if the fluid was transparent. Also the pump may include a detector to detect for the presence of air in the fluid line if the fluid was opaque, such as blood. However, the prior art air-in-line detectors included a manual control to set the detector to either detect air-in-line for the transparent fluid or for the opaque fluid. Such manual control of the detector could lead to an error on the part of the operator so that the detector may be improperly set. Unfortunately, an improper air-in-line detection of air-in-line could result in serious consequences for the patient.

The present invention overcomes the difficulties of the prior art by providing for an automatic detection of the type of fluid in the line so as to determine whether the fluid is an opaque fluid such as blood or a transparent fluid such as a drug solution. In addition to the detection of the type of fluid in line, the detector also provides for an alarm upon the appearance of air in the fluid line no matter what type of fluid is present in the line. In addition, the present invention provides for a number of fail-safe safety features so as to provide for an alarm if the detector is not operating properly. For example, if the detector does not detect either an opaque or a transparent fluid in the fluid line, the alarm is automatically actuated. Also, if any of the detector elements or the wiring or the grounding of the system is improper, the detector automatically goes into an alarm condition.

The present invention thereby provides for an automatic air-in-line fluid detector for detecting air-in-line no matter whether the fluid in the line is transparent or opaque and by providing for such automatic detection the present invention eliminates operator error to ensure a proper infusion of fluid to a patient.

A clearer understanding of the invention will be had with reference to the following description and drawings wherein FIG. 1 illustrates a volumetric infusion pump showing a suspended bottle of fluid to be infused and with the pump including an automatic air-in-line fluid detector of the present invention.

FIG. 8 is a schematic of the automatic air-in-line fluid detector of the present invention.

Figure 1:
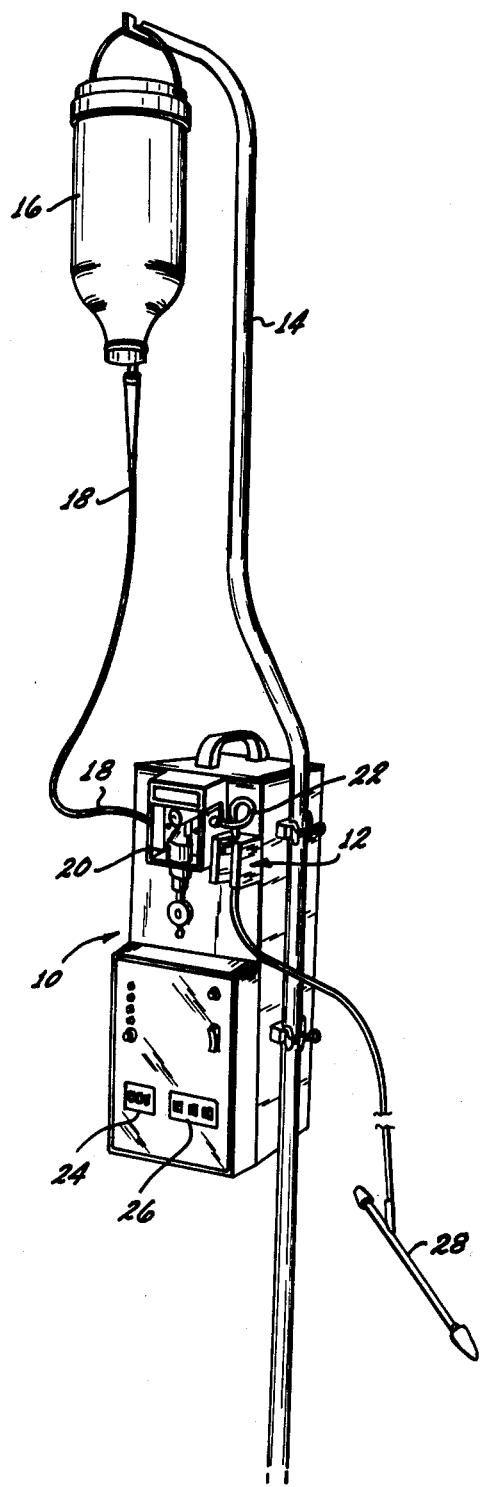
Figure 2:
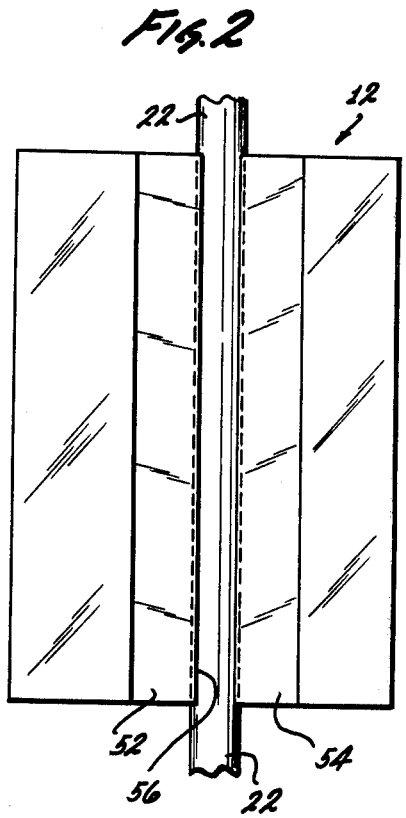
FIG. 2 illustrates a front view of an external portion of the automatic detector of the present invention which portion receives the fluid line.

In FIG. 1 a volumetric pump 10 is shown, which volumetric pump may include an automatic air-in-line fluid detector having an external detector portion 12 for receiving a fluid line. The pump 10 is mounted on a pole 14 and a bottle of fluid 16 to be infused is supported above the pump 10. Fluid from the bottle 16 is allowed to flow downward by gravity through a fluid line 18 and enters a disposable cassette 20. The pump provides for an accurate pumping of the fluid from the cassette 20 to an outside fluid line 22.

For example, the pump 10 may include a pair of dials such as dials 24 and 26 which control the rate of fluid flow to the fluid line 22 and the volume of fluid which is to flow through the line 22 to the patient. At the end of the line 22 is provided means 28 for allowing of the infusion of the fluid to the patient; for example, the means 28 may include a hypodermic needle which is used to infuse fluid into the vein of the patient. The pump 10 may be of the type shown in U.S. Ser. No. 473,901 filed 5/28/74, U.S. Pat. No. 3,985,133, which application is assigned to the same assignee as the instant application. It is to be appreciated, however, that the automatic air-in-line fluid detector of the present invention may be used with other types of fluid pumps or any means of infusing fluid to a patient such as gravity feed.

The fluid line 22 passing from the cassette 20 is positioned within a channel in the external fluid detector portion 12. The external fluid detector 12 includes a plurality of detector elements which in combination with appropriate electronic circuitry provides for an automatic detection between an opaque fluid or a transparent fluid in the fluid line and with a detection of air-in-line for either the opaque fluid or the transparent fluid.

FIGS. 2 through 7 show the details of the construction of the external fluid detector portion 12. The detector portion 12 includes a body member 50 having an open front with a pair of tapered sides 52 and 54 leading to a circular channel 56 which channel receives the fluid line 22. A plurality of light emitters and light detectors are disposed along the channel 56 on opposite sides of the channel so as to provide for the detection of either an opaque or transparent fluid and with a further detection of air-in-line for either type of fluid.

The plurality of light emitters are positioned in openings 58 through 66 in the body member 50 and with these openings communicating with one side of the channel 56. The body member 50 is also provided with a recess portion 68 so as to provide access to the openings 58 through 66 to properly position the light emitters and to provide for the electrical wiring to the light emitters. These light emitters may be light emitting diodes and provide for a light output spectrum in the infrared range. Since certain drugs are light sensitive, the infrared light spectrum provides for a proper detection without damaging the drug solutions. The light emitters positioned in openings 60 and 62 in association with light detectors provide for the detection of the air-in-line of the transparent fluid and the light emitters positioned in openings 58, 64, and 66 in association with light detectors provide for the detection of air-in-line of the opaque fluid such as blood.

On the opposite side of the channel 56 a plurality of light detectors such as phototransistors having a light detection spectrum complementary to the light emitters are positioned in a plurality of openings 70 through 78. These openings communicate between a recessed area 80 in the body 50 and the channel 56. The detectors positioned in openings 72 and 74 provide for the detection of air-in-line in the transparent fluid and the detectors positioned in the openings 70, 76, and 78 provide for the detection of air-in-line in the opaque fluid such as blood.

Figure 7:
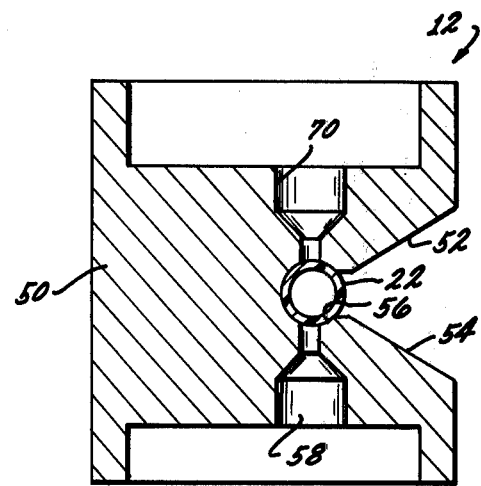
FIG. 7 illustrates a cross-sectional view of the portion of the automatic detector taken along lines 7—7 of FIG. 3.

It should be noted that the emitters and detectors relating to the detection of air-in-line for the opaque fluid are along the same axis, such as shown in FIG. 7, so that if an opaque fluid is present in the fluid line 22 positioned in the channel 56, little or no light energy passes from one of the emitters to one of the detectors. If, on the other hand, a transparent fluid or air is present in the fluid line 22 positioned in the channel 56, light energy freely passes from an emitter to its complementary detector arranged as shown in FIG. 7. The emitters and detectors positioned in openings 64, 66, 76, and 78 are arranged along the same axis in the same way as that shown in FIG. 7.

Figure 5:
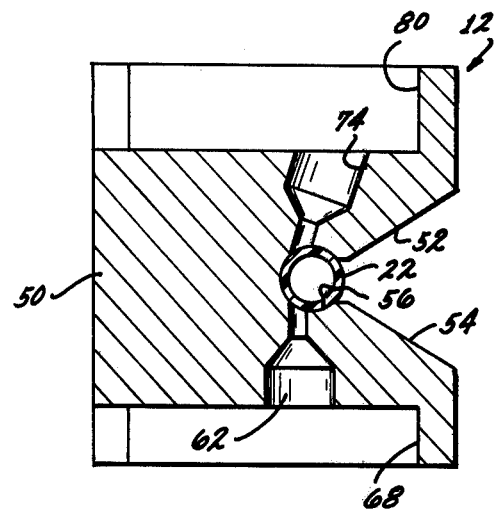
FIG. 5 illustrates a cross-sectional view of the portion of the automatic detector taken along lines 5—5 of FIG. 3.
Figure 6:
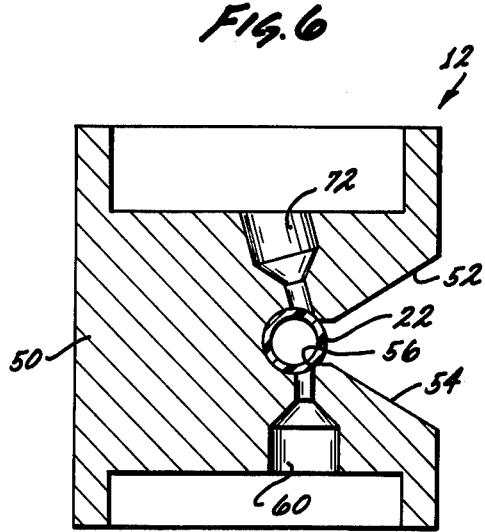
FIG. 6 illustrates a cross-sectional view of the portion of the automatic detector taken along lines 6—6 of FIG. 3.

The emitters and detectors used to provide for the detection of air-in-line in the transparent fluid as shown in FIGS. 5 and 6 are offset from each other. Specifically with reference to FIG. 5, the emitter in opening 62 is arranged to direct light energy through the channel 56 but at a rearward position of the channel 56. In addition, the detector is set at an angle. When there is a transparent fluid in the line 22, the light from the emitter in the opening 62 is refracted to pass into the detector in the opening 74. However, if there is air in the tube 22, the light is not refracted and passes directly through the line 22 and not to the detector in the opening 74. The operation of the emitter and detector in the openings 60 and 72 shown in FIG. 6 are essentially similar to that shown in FIG. 5 and described above except they are located to the front of the channel 56. The positioning of these emitters and detectors ensures detection on both sides of the fluid line 22 and enables the detector to pass small air bubbles which are not harmful but detect larger air bubbles.

Figure 3:
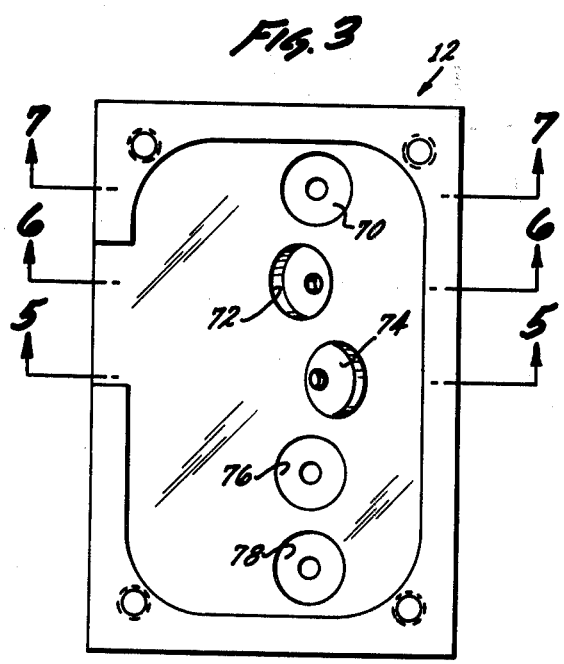
FIG. 3 illustrates a left side view of the portion of the automatic detector of FIG. 2.
Figure 4:
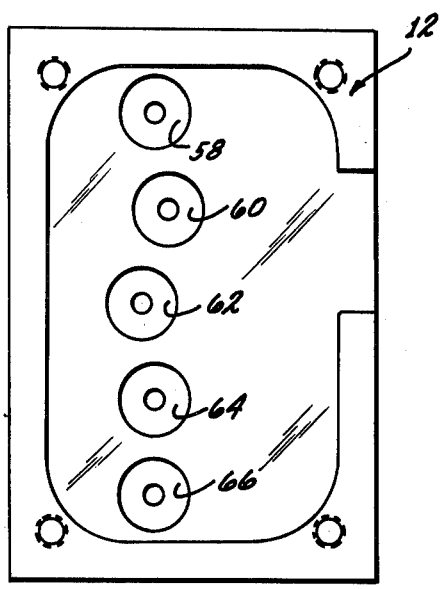
FIG. 4 illustrates a right side view of the portion of the automatic detector of FIG. 2.

FIG. 8 illustrates a schematic of the electrical system which provides for the automatic detection of transparent fluid or opaque fluid in the line 22 and, in addition, provides for detection of air-in-line no matter what type of a fluid is present in the fluid line. In FIG. 8, a plurality of light emitters such as infrared LEDs 100 through 108 are shown and these light emitters are positioned within the openings 58 through 66 shown in FIG. 4. In addition, a plurality of light detectors such as phototransistors 110 through 118 are used to detect the presence or absence of light from the light emitters and with such phototransistors positioned in the openings 70 through 78 as shown in FIG. 3.

The light emitters 100, 106, and 108 are in parallel and are supplied with a positive source of voltage and with the light emitters being grounded through resistors 120 and 124. An output signal is taken across the resistors 120 through 124 and supplied as three individual inputs to a NAND gate 126. When the light emitters 100, 106, and 108 are operating properly, and thereby producing light energy, a HIGH signal, taken across the resistors 120 through 124, is supplied to the NAND gate 126 representing the proper operation of each of the light emitters. In addition, the NAND gate 126 receives another input signal, which will be described in a later portion of this application, which signal represents the proper or improper grounding of the system. All of the signals applied to the NAND gate 126 must be HIGH so as to provide for a LOW output signal from the NAND gate 126, which LOW output signal indicates that the wiring is proper, and that the light emitters 100, 106, and 108 used as part of the air-in-line detection system for opaque fluid are properly operating.

The light emitters 102 and 104 are in series and are also supplied with a positive voltage, and with the light emitters 102 and 104 also grounded. The grounding system for the emitters 102 and 104 are part of the input signals to a NOR gate 128. The NOR gate 128 includes a pair of inputs one of which represents the main ground for the system. If either of the inputs to the NOR gate 128 goes HIGH, then the output of the NOR gate 128 goes LOW to provide for a LOW input to NAND gate 126 which, as indicated above, provides an output from the NAND gate 126 representing an alarm condition. For example, if the main ground is broken, then the input to the NOR gate 128 through the resistor 130 goes HIGH to provide for a LOW output from the NOR gate 128. Also, if the light emitters 102 or 104 or if any of the detectors 110 through 118 fail or if the wiring is broken, this also provides for a HIGH input to the NOR gate 128 to produce an alarm signal from the NAND gate 126.

The individual phototransistors 110 through 118 include individual resistors 132 through 140 between their base and emitter junctions and with the emitters all grounded through the main ground. In addition, the individual phototransistors 110 through 118 have their collectors biased with positive voltage through resistors 142 through 150. The light energy passing between the light emitters 100 through 108 and the light detectors 110 through 118 controls the current flow through the light detectors 110 through 118. The greater the amount of light energy passed to the light detector, the greater the current flow through the light detector. If little or no light energy is passed to a light detector, then the collector of the light detector remains HIGH. If a sufficient amount of light energy is passed to a light detector, then the collector is pulled towards ground and the output at the collector is pulled LOW. Therefore, a LOW output at the collector represents a passage of light and a HIGH output at the collector represents the absence of light.

The three outputs from the detectors 110, 116, and 118, used for the detection of an opaque fluid in the fluid line are applied to a NOR gate 152. In addition, the outputs are individually applied to NOR gates 154, 156, and 158. The two outputs from the detectors 112 and 114, used for the detection of the transparent fluid in the fluid line, are applied as the inputs to a NAND gate 160 and as individual inputs to NAND gates 162 and 164. The output from the detector 110, which is the first detector to see the fluid in the line, provides a preconditioning of the operation of the system since this detector initially discriminates between an opaque or transparent fluid in the fluid line.

If there is either a transparent fluid in the fluid line 22 or if there is air in the line, then the output of the NOR gate 152 is HIGH since all the inputs to the NOR gate would be LOW. The gate 152 is therefore used as a steering gate to control the NAND gates 162 and 164 to operate in response to either transparent fluid in the line or air in the line. If there is a transparent fluid in the fluid line 22, then the inputs to the NAND gates 162 and 164 from the detectors 112 and 114 would be low, so that the output from the gates 162 and 164 would be HIGH which is an indication of no air in the line. If, on the other hand, the fluid line 22 includes a transparent fluid but there is an air bubble in the line sufficiently large to overlap both detectors 112 and 114, then the inputs to the NAND gates 162 and 164 from these detectors would be HIGH which would, in turn, provide for a LOW output at the output of the detectors 162 and 164.

The outputs from the NAND gates 162 and 164 are applied to a NOR gate 166 and both inputs to the NOR gate 166 must be LOW in order to get a HIGH output which HIGH output represents air in the transparent fluid line. If a small air bubble is present in the transparent fluid line which air bubble does not overlap both detectors 112 and 114, then only one of the inputs to the NAND gates 162 and 164 would be HIGH so that only one of the inputs to the NOR gate 166 would be low. The system of the present invention, therefore, automatically allows for the passage of small air bubbles without alarm but provides for the detection of large air bubbles with alarm and with the longitudinal distance between the emitter 102 with its corresponding detector 112 and the emitter 104 with its corresponding detector 114 determining the minimum size of the air bubble which can be detected.

If there is a failure in the system affecting any of the emitters 102 and 104 or the detectors 112 and 114, then this failure automatically provides for a HIGH input to one of the NAND gates 162 or 164. In this way, a failure makes the system more sensitive since the remaining emitter-detector pair will sense every air bubble no matter what its size to provide for a HIGH input to the other one of the NAND gates 162 or 164 and with a resultant high output from the NOR gate 166.

The output from the NAND gate 160 is applied as the second input to each one of the NOR gates 154, 156, and 158. The NAND gate 160 controls or steers the detection of air-in-line when an opaque fluid such as blood is in the fluid line 22. Assuming an opaque fluid such as blood in the fluid line 22, then the input to the NAND gate 160 from the detectors 112 and 114 are both HIGH so as to provide a LOW input to each one of the NOR gates 154, 156, 158. When there is no air-in-line, the other input to the NOR gates 154, 156, and 158 from the detectors 110, 116, and 118 are HIGH so that if there is no air-in-line all of the NOR gates 154, 156, and 158 provide for LOW outputs.

Three NAND gates 168, 170 and 172 each receive different sets of inputs from the outputs from the NOR gates 154, 156, and 158. If there is no air-in-line for the opaque fluid in the fluid line, then all of the inputs to the NAND gates 168, 170, and 172 are LOW thereby providing for HIGH outputs which are applied to a NAND gate 174. If, however, there is air-in-line and this air is of sufficient size so as to overlap two of the etectors 110, 116, and 118, then two of the gates 154, 156, and 158 will provide a HIGH output. Any two of the gates 154, 156, and 158 will provide that one of the NAND gates 168, 170, and 172 will produce a LOW output and any LOW output to the NAND gate 174 provides for a HIGH output from the NAND gate 174.

If, however, there is a small air bubble in the opaque fluid line so as to provide for the passage of light energy to only one of the detectors 110, 116, and 118 at a time, then only one of the NOR gates 154, 156, and 158 at a time will go HIGH. If only one of these gates at a time goes HIGH, then there will not be simultaneous HIGH inputs to the individual NAND gates 168, 170, and 172 and, therefore, none of the outputs of these gates will go LOW.

The NOR gate 166, as indicated above, provides for a HIGH output if there is an air bubble in the transparent fluid line sufficient in size to provide that both NAND gates 162 and 164 provide LOW outputs. The output from the NOR gate 166 is applied to a NAND gate 176 which NAND gate has a LOW output representing air-in-line when the input to the NAND gate is HIGH. The output from the NAND gate 176 is also applied as an input to the NAND gate 174, so that any LOW input to the NAND gate 174 represents air-in-line for either a transparent fluid or an opaque fluid in the fluid line. The gates 152 and 160 steer the control of the detection of air-in-line to the appropriate portion of the circuitry.

When the steering of the air-in-line detection by the control gates 152 and 160 is not proper, this is represented by signals from both gates 152 and 160. The signals from the gates 152 and 160 are also applied to a NAND gate 178, directly in the case of the output from the gate 160 and through an inverter 180 in the case of the output from the gate 152. If both signals to the NAND gate 178 are HIGH, this represents that the control gates 152 and 160 are not operating properly since this signal condition represents that both transparent and opaque fluid control signals are present. The output from the gate 178 is passed through an inverter 182 as one input to a NOR gate 184. NOR gate 184 also receives as an input the output from the NAND gate 126 and also as an input the output from the NAND gate 174. Any HIGH input to the NOR gate 184 represents an alarm condition represented by a LOW output from the NOR gate. If the system is operating properly with no failures and with no detectible air-in-line, then the output from the NOR gate 184 is HIGH to represent proper operation of the system with no air-in-line.

If any input to the NOR gate 184 is HIGH input so as to produce a LOW at the output this, as indicated above, represents an alarm condition. The output from the NOR gate 184 is coupled to the base of a transistor 186 through a resistor 188. When the output of the NOR gate 184 is LOW, the transistor 186 turns off to produce a HIGH output across a capacitor 190. This HIGH output in turn sets off an alarm such as an audible and/or visible alarm 192 and may also discontinue the operation of the pump.

It can be seen, therefore, that the automatic air-in-line fluid detection system of the present invention provides for the detection of either a transparent or an opaque fluid in the fluid line and with this detection then controlling appropriate portions of the light detector system to provide for detection of air-in-line.

Assuming the case when there is a clear or transparent fluid in the fluid tube 22, then the detectors responsive to opaque fluid in the line cannot discriminate between air or clear fluid in the fluid line. However, in such a case, the detectors responsive to transparent fluid in the line can discriminate between transparent fluid and air in the line so as to provide for the detection of air within the transparent fluid in the line.

In the alternative situation when there is opaque fluid in the line, such as blood, then the detectors responsive to transparent fluid cannot discriminate between air or opaque fluid in the line. However, the detectors responsive to opaque fluid can discriminate between air and opaque fluid in the line so as to provide for the detection of air in the opaque fluid in the line.

In addition to the above, the present invention includes a plurality of additional safeguards for providing for an alarm condition when the system is not operating properly. For example, if any of the light emitters or detectors fail, then the system either alarms or becomes more sensitive. If the ground fails, then the system alarms. If the system fails so as to not provide for outputs representing either an opaque or a clear fluid, then the system alarms. All of these various safeguards, therefore, ensure that in the event the system is not operating properly, an alarm condition is sounded and the pump may be stopped so that the system can be either cleared or repaired or taken out of operation until the system can be made to operate properly.

Although the invention has been described with reference to a particular embodiment, it should be appreciated various adaptations and modifications may be made and the invention is only to be limited to the appended claims.

I claim:

1. An automatic fluid detector for detecting the presence of air in a fluid line containing either an opaque or a transparent fluid, including
    means for supporting a portion of the fluid line for detection of air in the fluid line,
    first means operatively coupled to the supported portion of the fluid line and responsive to the fluid line containing air or the opaque fluid for producing a first signal in accordance with the fluid line containing air or the opaque fluid and responsive to the fluid line containing the transparent fluid for producing a second signal in accordance with the fluid line containing the transparent fluid,
    second means operatively coupled to the supported portion of the fluid line and responsive to the fluid line containing the opaque fluid for producing a first signal in accordance with the fluid line containing the opaque fluid and responsive to the fluid line containing air or the transparent fluid for producing a second signal in accordance with the fluid line containing air or the transparent fluid,
    third means operatively coupled to the first and second means and responsive to the first means producing the first signal for passing the first and second signals from the second means, and
    fourth means operatively coupled to the first and second means and responsive to the second means producing the second signal for passing the first and second signals from the first means.

2. The automatic fluid detector of claim 1 wherein the first and second means each include at least two optical detectors spaced from each other and with the detection of air in the opaque or transparent fluid dependent on at least two of the optical detectors included in either the first or second means detecting the presence of air at the same time.

3. The automatic fluid detector of claim 2 wherein a failure of any of the optical detectors provides for a detection of air in the fluid line by the remaining detectors included in either the first or second means.

4. The automatic fluid detector of claim 2 wherein the first means includes two optical detectors and the second means includes three optical detectors and with the of air by the second detection means dependent on the detection of air in the fluid line by any two of the three optical detectors.

5. The automatic fluid detector of claim 4 wherein one of the three optical detectors included in the second means is located at an initial position to initially detect the fluid in the fluid line and wherein the two optical detectors included in the first means are located after the one optical detector and wherein the remaining two of the three optical detectors included in the second detectors are located after the two optical detectors included in the first means.

6. The automatic fluid detector of claim 1 additionally including alarm means coupled to the first and second means for producing an alarm in accordance with the detection of air in the fluid line.

7. The automatic fluid detector of claim 6 additionally including means for producing an alarm in accordance with a failure in portions of the detector system.

8. The automatic fluid detector of claim 6 additionally including means coupled to the third and fourth means for producing an alarm when the third and fourth means pass signals from both the first and second means.

9. An automatic air-in-line fluid detector for detecting air-in-line fluid detector for detecting the presence of air-in-line for a fluid line containing either a transparent or an opaque fluid, including
    first means operatively coupled to the fluid line for detecting air-in-line with the fluid line containing the transparent fluid,
    second means operatively coupled to the fluid line for detecting air-in-line with the fluid line containing the opaque fluid, and
    third means operatively coupled to the first and second means and responsive to the fluid line containing the transparent fluid or the opaque fluid and with the first means detecting air-in-line in the fluid line containing the transparent fluid when the third means is responsive to the fluid line containing the transparent fluid and with the second means detecting air-in-line when the third means is responsive to the fluid line containing the opaque fluid.

10. The automatic air-in-line fluid detector of claim 9 wherein the first and second means each include at least two optical detectors spaced from each other and with the detection of air in the opaque or transparent fluid dependent on at least two of the optical detectors included in either the first or second means detecting the presence of air at the same time.

11. The automatic air-in-line fluid detector of claim 10 wherein a failure of any of the optical detectors provides for a detection of air in the fluid line by the remaining detectors included in either the first or second means.

12. The automatic air-in-line fluid detector of claim 10 wherein the first means includes two optical detectors and the second means includes three optical detectors and with the of air by the second detection means dependent on the detection of air in the fluid line by any two of the three optical detectors.

13. The automatic air-in-line fluid detector of claim 12 wherein one of the three optical detectors included in the second means is located at an initial position to initially detect the fluid and wherein the two optical detectors included in the first means are located after the one optical detector and wherein the remaining two of the three optical detectors included in the second means are located after the two optical detectors included in the first means.

14. The automatic air-in-line fluid detector of claim 9 additionally including alarm means coupled to the first and second means for producing an alarm in accordance with the detection of air in the fluid line.

15. The automatic air-in-line fluid detector of claim 14 additionally including means for producing an alarm in accordance with a failure in portions of the detector system.

16. An automatic air-in-line fluid detector for detecting the presence or absence of air in either a transparent or an opaque fluid in a fluid line, including
   a first plurality of optical detectors operatively coupled to the fluid line for detecting the presence or absence of air-in-line with the fluid line containing transparent fluid and with the first plurality of optical detectors producing first signals in accordance with the presence of air-in-line and producing second signals in accordance with the absence of air-in-line,
   a second plurality of optical detectors operatively coupled to the fluid line for detecting the presence or absence of air-in-line with the fluid line containing opaque fluid and with the second plurality of optical detectors producing first signals in accordance with the presence of air-in-line and producing second signals in accordance with the absence of air-in-line, and
   means responsive to the first and second signals from the first and second plurality of optical detectors for determining the presence of either transparent or opaque fluid in the fluid line and for passing the first and second signals from the first plurality of optical detectors with the fluid line containing the transparent fluid and for passing the first and second signals from the second plurality of optical detectors with the fluid line containing the opaque fluid.

17. The automatic air-in-line fluid detector of claim 16 wherein the first and second plurality of optical detectors each include at least two optical detectors spaced from each other and with the detection of air in the fluid line containing either opaque or transparent fluid dependent on at least two of the optical detectors included in either the first or second plurality of optical detectors detecting the presence of air at the same time.

18. The automatic air-in-line fluid detector of claim 17 wherein a failure of any of the optical detectors provides for a detection of air in the fluid line by the remaining detectors included in either the first or second plurality of optical detectors.

19. The automatic air-in-line fluid detector of claim 16 wherein the first plurality of optical detectors includes two optical detectors and the second plurality of optical detectors includes three optical detectors and with the detection of air in the fluid line by the second plurality of optical detectors dependent on the detection of air in the fluid line by any two of the three optical detectors.

20. The automatic air-in-line fluid detector of claim 19 wherein one of the three optical detectors included in the second plurality of optical detectors is located at an initial position to initially detect the presence of transparent or opaque fluid in the fluid line and wherein the two optical detectors included in the first plurality of optical detectors are located after the one optical detector and wherein the remaining two of the three optical detectors included in the second plurality of optical detectors are located after the two optical detectors included in the first plurality of optical detectors.

21. The automatic air-in-line fluid detector of claim 9 additionally including alarm means responsive to the first signals from the first and second optical detectors for producing an alarm in accordance with the presence of air in the fluid line.

22. The automatic air-in-line fluid detector of claim 21 additionally including means for producing an alarm in accordance with a failure in portions of the detector system.

23. The automatic air-in-line fluid detector of claim 21 additionally including additional means coupled to the means responsive to the signals from the first and second plurality of optical detectors for producing an alarm when the means responsive to the signals from the first and second plurality of optical detectors passes signals from both the first and second plurality of optical detectors.

* * * * *